(12) United States Patent
Costa et al.

(10) Patent No.: US 10,683,476 B2
(45) Date of Patent: Jun. 16, 2020

(54) METHOD AND APPARATUS TO PREPARE CARDIAC ORGANOIDS IN A BIOREACTOR SYSTEM

(71) Applicant: Icahn School of Medicine at Mount Sinai, New York, NY (US)

(72) Inventors: Kevin David Costa, New York, NY (US); Timothy James Cashman, New York, NY (US); Peter Constantine Backeris, Union City, NJ (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 430 days.

(21) Appl. No.: 15/314,870

(22) PCT Filed: May 29, 2015

(86) PCT No.: PCT/US2015/033206
§ 371 (c)(1),
(2) Date: Nov. 29, 2016

(87) PCT Pub. No.: WO2015/184273
PCT Pub. Date: Dec. 3, 2015

(65) Prior Publication Data
US 2017/0107469 A1    Apr. 20, 2017

Related U.S. Application Data

(60) Provisional application No. 62/004,467, filed on May 29, 2014.

(51) Int. Cl.
*C12M 3/00* (2006.01)
*C12M 1/00* (2006.01)
*C12M 1/42* (2006.01)

(52) U.S. Cl.
CPC ............ *C12M 21/08* (2013.01); *C12M 23/00* (2013.01); *C12M 23/26* (2013.01); *C12M 23/38* (2013.01); *C12M 35/02* (2013.01)

(58) Field of Classification Search
CPC ...... C12M 21/08; C12M 23/00; C12M 23/26; C12M 23/38; C12M 35/02
See application file for complete search history.

(56) References Cited

U.S. PATENT DOCUMENTS

| | | |
|---|---|---|
| 2002/0106625 A1 | 8/2002 | Hung et al. |
| 2010/0249491 A1 | 9/2010 | Farnan et al. |
| 2014/0030762 A1 | 1/2014 | Deplano et al. |

OTHER PUBLICATIONS (Iyer, RK et al.) Spatiotemporal Tracking of Cells in Tissue Engineered Cardiac Organoids. Journal of tissue engineering and regenerative medicine. 3.3 (2009): 196. abstract; section 2.4, 1st paragraph. Mar. 2009.

(Continued)

*Primary Examiner* — William H. Beisner
*Assistant Examiner* — Danielle B Henkel
(74) *Attorney, Agent, or Firm* — Leason Ellis LLP

(57) ABSTRACT

A bioreactor system for preparing a cardiac organoid chamber and for subsequent testing thereof is described herein and shown in the exemplary drawing figures. The bioreactor system includes a first vessel having a hollow interior and an open top. A first cover is mated with the open top of the first vessel. The first cover has a first opening formed therein. The system further includes a cannula having a lumen that extends from an open first end to an open second end. The cannula is disposed within the first opening of the first cover such that a portion of the cannula lies below the first cover and for insertion into the hollow interior of the first vessel. A porous ring is coupled to the cannula at or proximate the open second end thereof. The system also includes a balloon catheter having an inflatable balloon at a distal end of a (Continued)

catheter shaft. The balloon catheter is adapted to pass through the lumen of the cannula when the balloon is in a deflated state. The balloon catheter is axially adjustable within the lumen to allow the balloon in an inflated state to be disposed adjacent: (1) the open second end of the cannula; and (2) the porous ring for preparing the cardiac organoid chamber about the inflated balloon and porous ring. The cannula and porous ring construction and combination allows for the balloon to be deflated and removed from the lumen of the cannula while the engineered cardiac organoid chamber remains attached to the porous ring. This permits the testing of organoid pump function, such as organoid pressure and volume characteristics, without having to transfer the engineered cardiac organoid from one tool (e.g., an incubation tool) to another tool (e.g., a functional testing apparatus).

22 Claims, 8 Drawing Sheets

(56) References Cited

OTHER PUBLICATIONS

Eun Jung Lee et al: "Engineered Cardiac Organoid Chambers: Toward a Functional Biological Model Ventricle", Tissue Engineering Part A, vol. 14, No. 2, Feb. 1, 2008 (Feb. 1, 2008), pp. 215-225, XP055460747, ISSN: 1937-3341, DOI: 10.1089/tea.2007.0351.

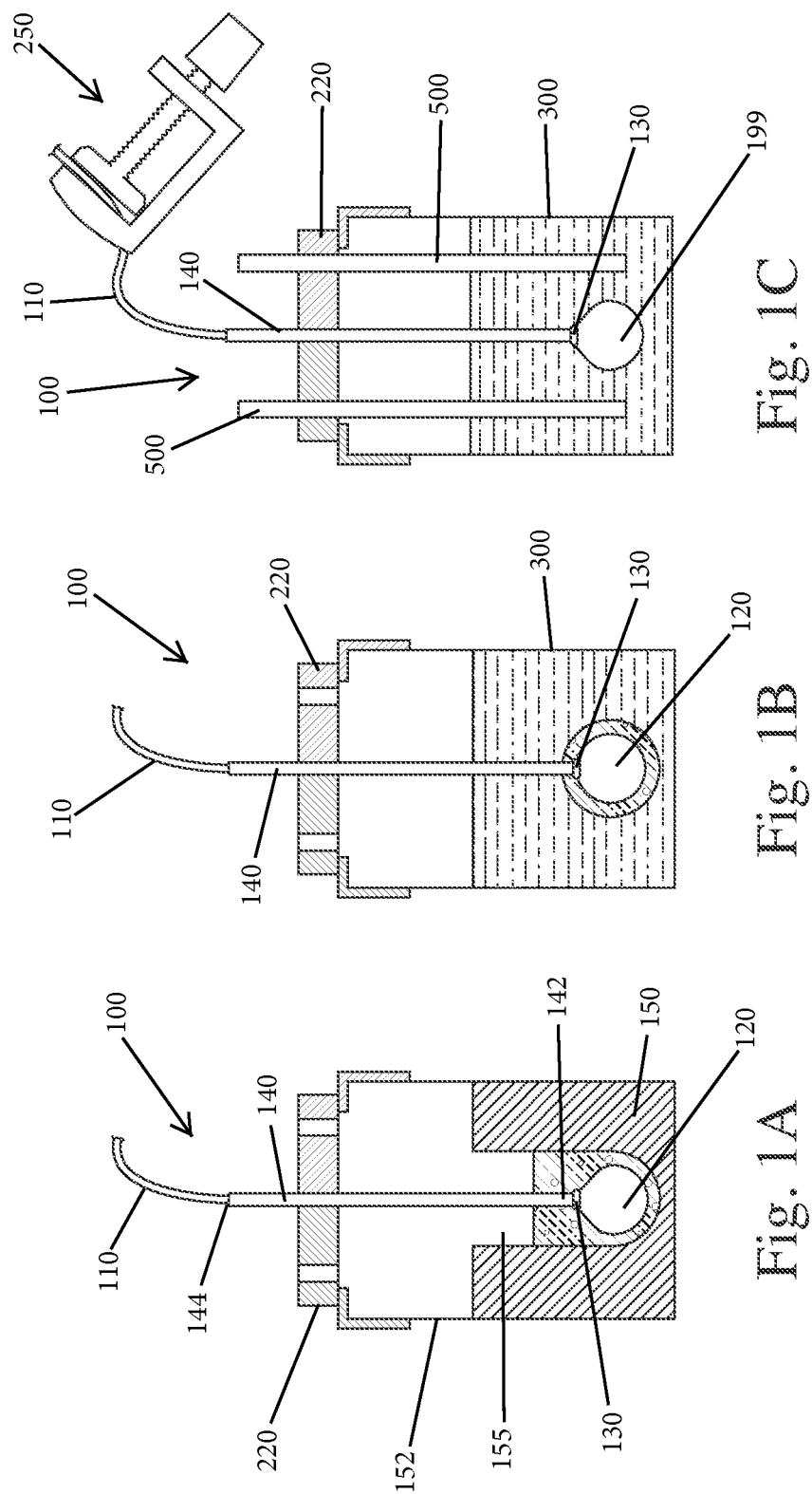

METHOD AND APPARATUS TO PREPARE CARDIAC ORGANOIDS IN A BIOREACTOR SYSTEM

CROSS-REFERENCE TO RELATED APPLICATION

The present application is a U.S. National Phase of International Patent Application PCT/US2015/033206, filed on May 29, 2015, which claims priority to U.S. patent application Ser. No. 62/004,467, filed May 29, 2014, the contents of each of which is hereby expressly incorporated by reference as if set forth in their respective entireties herein.

This invention was made with government support under grant numbers HL085826 and HHSN26820100 awarded by the National Institutes of Health. The government has certain rights in the invention.

TECHNICAL FIELD

The present invention is generally directed to an organoid bioreactor and more specifically, to an apparatus and method for engineering cardiac organoids (organoid chambers) from a cell source (e.g., human cells) with the apparatus being configured to pump fluid and mimic key aspects of natural heart pump function.

BACKGROUND

Repairing a damaged heart remains a major challenge since the human heart has only a limited capacity to regenerate itself and damage to the heart muscle usually results in irreversible cardiac dysfunction. Much research is ongoing to develop technologies that may allow the refurbishing of failing myocardium with new muscle. Many of the existing cardiac tissue constructs used for in vitro models are in the form of tissue strips or patches. These tissue strips and patches can be used to measure contractile force, but cannot directly generate the types of measures that cardiologists are trained to understand, such as volume, pressure, ejection fraction, and stroke work. More recently, techniques have been developed to produce cardiac tissue chambers (organoids) that can generate these types of measures, and these newer techniques require a number of complex steps.

For instance, techniques for creating a cardiac organoid typically require 1) introducing a cold cell-matrix solution into a an outer cup-shaped mold; 2) inflating a balloon catheter in the cell-matrix solution to a desired chamber size to form the inner mold boundary; 3) placing a small ring above the balloon contacting the cell-matrix solution to prevent tissue slippage during culture; 4) removing the outer cup-shaped mold after a specified time period, such as 24 hours; 5) incubating the remaining cell-matrix solution with the balloon catheter for a specified time period, such as 7 to 10 days, during which the engineered cardiac tissue (organoid) would form a coordinated network compacted around the balloon; 6) carefully deflating the balloon and removing the organoid from the deflated balloon catheter following the incubation period; and 7) connecting the organoid to an isolated heart setup by suturing it to a fluid-filled cannula.

While these newer techniques have been effective in generating the types of measures that are important for cardiologists in evaluating the efficacy of the engineered cardiac tissue, they require the investigators to be very delicate with the organoid when removing the balloon catheter and suturing the organoid to the cannula so as to avoid damaging or compromising the structure of the organoid.

SUMMARY

A bioreactor system for preparing a cardiac organoid chamber and for subsequent testing thereof is described herein and shown in the exemplary drawing figures. The bioreactor system includes a first vessel having a hollow interior and an open top. A first cover is mated with the open top of the first vessel. The first cover has a first opening formed therein. The system further includes a cannula having a lumen that extends from an open first end to an open second end. The cannula is disposed within the first opening of the first cover such that a portion of the cannula lies below the first cover and for insertion into the hollow interior of the first vessel. A porous ring is coupled to the cannula at or proximate the open second end thereof. The system also includes a balloon catheter having an inflatable balloon at a distal end of a catheter shaft (e.g., a flexible tubular structure). The balloon catheter is adapted to pass through the lumen of the cannula when the balloon is in a deflated state. The balloon catheter is axially adjustable within the lumen to allow the balloon in an inflated state to be disposed adjacent: (1) the open second end of the cannula; and (2) the porous ring for preparing the cardiac organoid chamber about the inflated balloon and porous ring. The cannula and porous ring construction and combination allows for the balloon to be deflated and removed from the lumen of the cannula while the engineered cardiac organoid chamber remains attached to the porous ring. This permits the testing of organoid pump function, such as organoid pressure and volume characteristics, without having to transfer the engineered cardiac organoid from one tool (e.g., an incubation tool) to another tool (e.g., a functional testing apparatus), which can damage the organoid and compromise sterility and viability of the living tissue.

BRIEF DESCRIPTION OF THE DRAWINGS FIGURES

FIGS. 1A-C are schematic illustrations of cardiac organoid chamber culture system (bioreactor) showing in FIG. 1A tissue casting between inner silicone balloon and outer agarose mold for first 24 hours; tissue after removal of agarose mold and placement in a cell culture media as shown in FIG. 1B; and the entire bioreactor with carbon rods in place for electrical pacing as shown in FIG. 1C;

DETAILED DESCRIPTION OF CERTAIN EMBODIMENTS

Figure 4A:
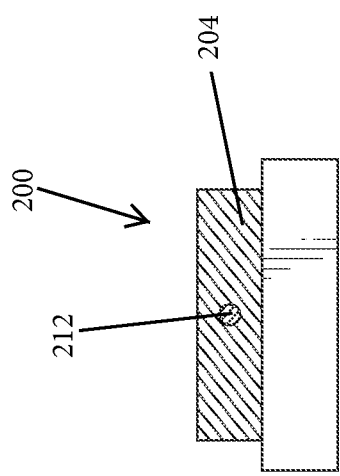
FIGS. 4A and 4B show side and top views, respectively, of an agarose mold jig.
Figure 4B:
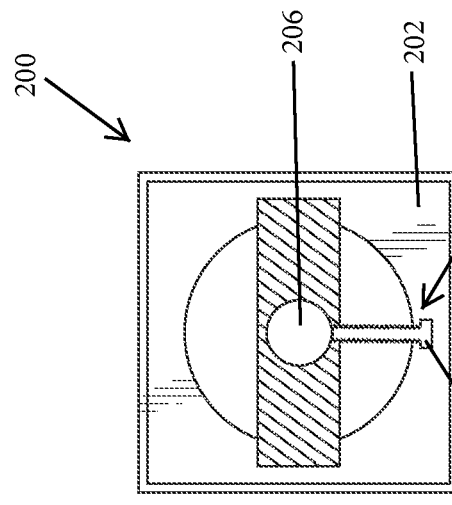

In accordance with the present invention, an apparatus and method are provided for preparing an engineered organoid structure and more specifically, for preparing a cardiac organoid (cardiac organoid chamber) using a bioreactor, with the organoid configured to pump fluid and mimic key aspects of natural heart pump function. Unlike the conventional engineering and testing techniques described herein, the apparatus and system of the present invention does not require removal of the cardiac organoid from one instrument and then placement of the engineered cardiac organoid on a second instrument for testing the organoid pump function. Appendix A sets forth a list of exemplary materials that can be used in the apparatus (bioreactor) and associated test equipment that are described herein.

Preparation of Engineered Cardiac Organoid Chambers

Referring to FIGS. 1-8, to create cell-populated cardiac organoid chambers, a bioreactor (system) 100 is used. As described herein, the bioreactor 100 is part of an overall system that is configured for testing the organoid function, including pump function, after the organoid is engineered in the bioreactor 100.

One exemplary bioreactor 100 is prepared as follows. A balloon catheter 110 is used in the bioreactor 100 and comprises an elongated shaft 112 that has a distal end 114. The shaft 112 can be in the form of a tubular structure that is flexible. The shaft 112 includes at least one lumen formed therein. At the distal end 114, an inflatable balloon 120 is disposed. The inflatable balloon 120 is in fluid communication with the lumen formed in the shaft 112 such that an inflation fluid can be delivered through the lumen or removed through the lumen or another lumen for changing the inflation characteristics of the balloon 120.

It will be appreciated that the shaft 112 can extend through the balloon 120 to provide additional support and in this embodiment the balloon 120 surrounds the distal end of the shaft. Alternatively, the balloon 120 can be unsupported and be sealingly attached to the distal end of the shaft 112 such that at least a portion of the balloon 120 is unsupported and spaced from the shaft 112.

The catheter 110 can be constructed by modifying an existing balloon catheter, such as a flexible Foley catheter. In particular, the distal tip that is typically found in Foley catheters can be removed. When the tip of the catheter is cut off, the bottom of the balloon 120 is flush with the end of the catheter shaft 112. The open cut end of the shaft can be sealed with an appropriate material, such as silicone (caulking).

A first ring (porous ring) 130 is used during the cell culturing process as described below. The first ring 130 can be in the form of a hydrophilic porous polyethylene ring. The first ring 130 is for use with a first cannula 140. The first cannula 140 is in the form of an elongated cannula that has a distal end 142 and an opposite proximal end 144. The first cannula 140 is formed of a suitable biocompatible material that will not corrode, rust, degrade, dissolve, etc., in the culture media that is used in the bioreactor 100. In addition, the first cannula 140 is formed of a material that can be easily sterilized, such as by autoclave, UV exposure, etc.

In one embodiment, the first cannula 140 is a 9-gauge stainless steel tube of predetermined length (e.g., about 8 cm) and having a predetermined width (e.g., an outer diameter (O/D) of about 0.15 inch and an inner diameter (I/D) of about 0.12 inch).

Figure 9:
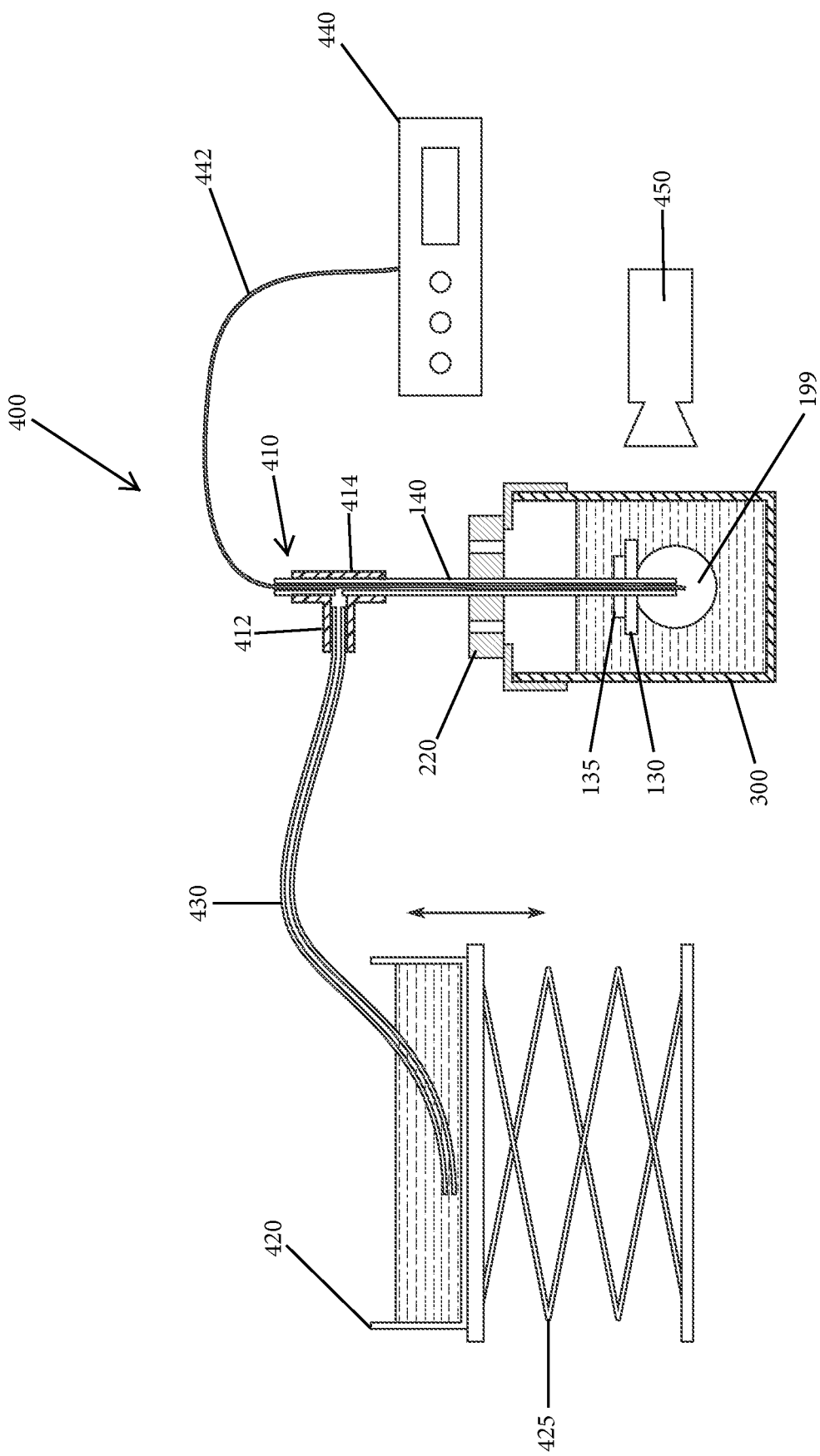
FIG. 9 is a schematic of an exemplary organoid function testing system.

The first ring 130 is centered on the cannula 140 and an O-ring 135 is preferably used in combination with the first ring 130 (See, FIG. 9). The O-ring 135 is formed of a suitable material, such as rubber. The O-ring 135 is placed on the cannula 140 and the first ring 130 is arranged such that it is disposed at the distal end of the cannula 140. The O-ring 135 is pushed down on top of the first ring 130 without displacing the first ring 130 from the distal end of the cannula 140. The O-ring 135 provides a water-tight seal to prevent fluid leakage.

It will be appreciated that the cannula 140 has sufficient rigidity to allow the inflated balloon 120 to be held in place at the distal end of the cannula 140 once the catheter 110 is inserted through the lumen of the cannula 140 and the balloon 120 is inflated as described below. In addition, the cannula 140 is sufficiently rigid such that it holds its shape and allows the insertion and removal of the catheter 110 from the lumen thereof and further is not deformed by the O-ring 135 which is sealingly disposed thereabout.

Preparation of the Mold

Figure 6:
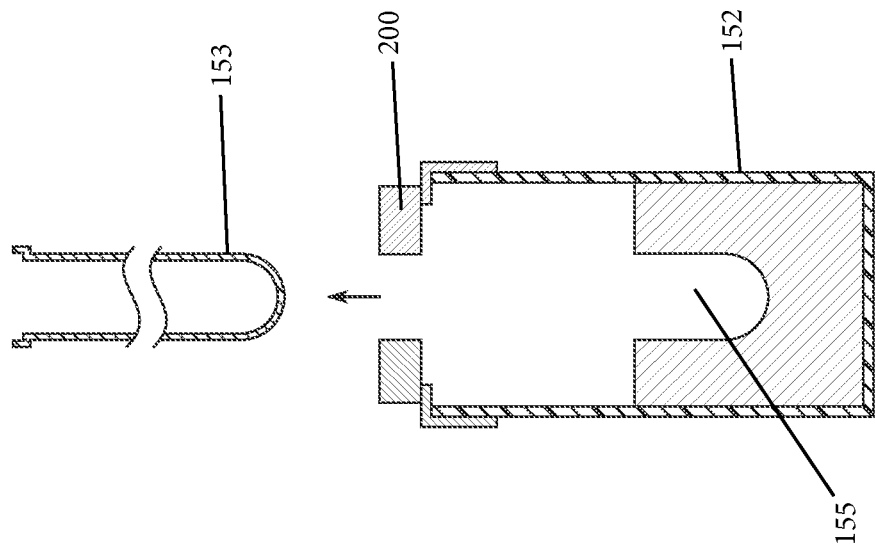
FIG. 6 is a cross-sectional view showing the agarose mold with the mandrel removed.
Figure 5:
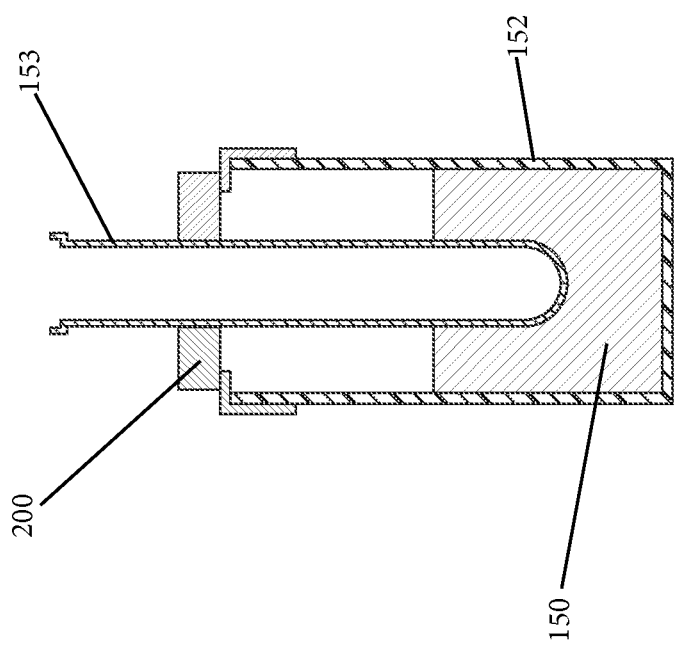
FIG. 5 is a cross-sectional view showing a mandrel (test tube) positioned with the agarose mold.

As shown in FIGS. 5-6, a mold 150 is prepared by preparing a suitable mold material which is then disposed within a first mold container (vessel) 152. The first mold container 152 has a hollow interior and can have a rectangular shape. A predetermined amount of the mold material is then added to the hollow interior of the first mold container 152. In one exemplary embodiment, the mold material is an Agarose hydrogel solution, such as a 2% Agarose solution, that provides structural support yet is permeable and non-adherent. In one embodiment, about 20 mls of the Agarose solution is added to the first mold container 152. The mold is then prepared by introducing a mandrel 153 into the mold material. The mandrel 153 can be in the form of a cylindrical structure with a hemispherical tip, such as a test tube (e.g., a 13 mm test tube). The mandrel 153 is centered within the first mold container 152 and is also positioned such that it is normal (perpendicular) to the mold material within the first mold container 152. It will be appreciated that one mandrel 153 forms one mold cavity when the molding process is complete and the mandrel is withdrawn.

As shown in FIGS. 4A, 4B, 5 and 6, the mandrel 153 can be suspended in the mold material using a first support member (cover) or first jig 200. The first jig 200 is designed to cover the first mold container 152 much like a shoe box cover covers the bottom of the box. However, it will be appreciated that other jig designs can be used in the present invention. The first jig 200 has a top surface 202 and side walls 204. The top surface 202 has an opening 206 formed therein, with the opening 206 being configured to receive the mandrel 153. The mandrel 153 can thus be supported by the first jig 200 such that the mandrel 153 can be locked in a desired position such that the desired spacing between the bottom of the mandrel 153 and the bottom of the first mold container 153 is achieved. The mandrel 153 can thus be slidingly moved within the opening 206 and a lock mechanism 210 can be used to lock the mandrel 153 in the desired position. For example, a first set screw 212 that extends through one side wall 204 can be used to secure the mandrel 153 in place within the mold material that is within the first mold container 152. To move the mandrel 153, the set screw 212 is loosened to allow axial movement of the mandrel 153 and when the mandrel 153 is in the desired position, the set screw 212 is tightened. Other locking mechanisms can be used.

In one embodiment, the mandrel is positioned within the mold material (Agarose solution) so that there is about 0.5 to 0.75 cm of the mold material between the bottom of the mandrel and the bottom of the first mold container 152. After the mold material has set, the mandrel is carefully removed from the mold material leaving a void (e.g., the imprint of the test tube) in the mold material. This void defines the formed mold cavity 155 which is cup-shaped (FIGS. 1A and 6). The mold formed within the first mold container 152 is then placed under a UV light or the like to sterilize the mold.

Additional steps can be performed to ready the mold for use. For example, about 1.5 ml of a sterile 2% BSA (bovine serum albumin) solution can be added to the mold and then the first mold container 152 is covered and the mold is incubated for a predetermined period of time (e.g., 1 hour at about 37° C.). After the incubation period is completed, the mold can be washed with one or more solutions including a phosphate-buffered saline and deionized water. In one embodiment, the wash process involves washing the mold three times with a phosphate buffered saline solution and one time with deionized water. The deionized water is then removed from the mold and the mold is allowed to dry.

The mold 150 can thus be formed of 2% agarose in phosphate-buffered saline (PBS).

Figure 3A:
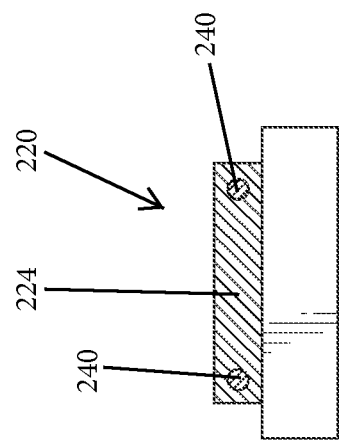
FIGS. 3A and 3B show side and top views, respectively, of a cannula/electrode jig.
Figure 3B:
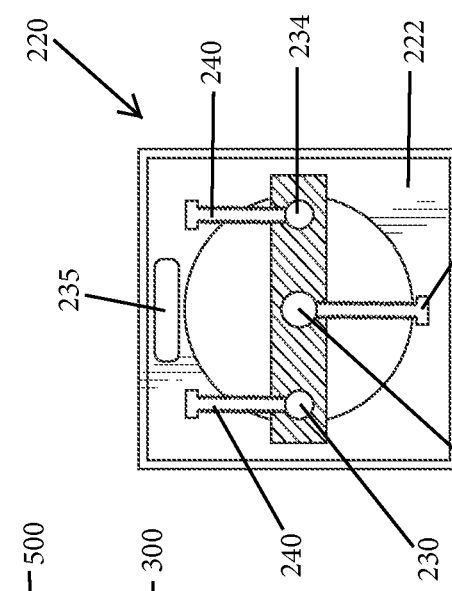
Figure 2:
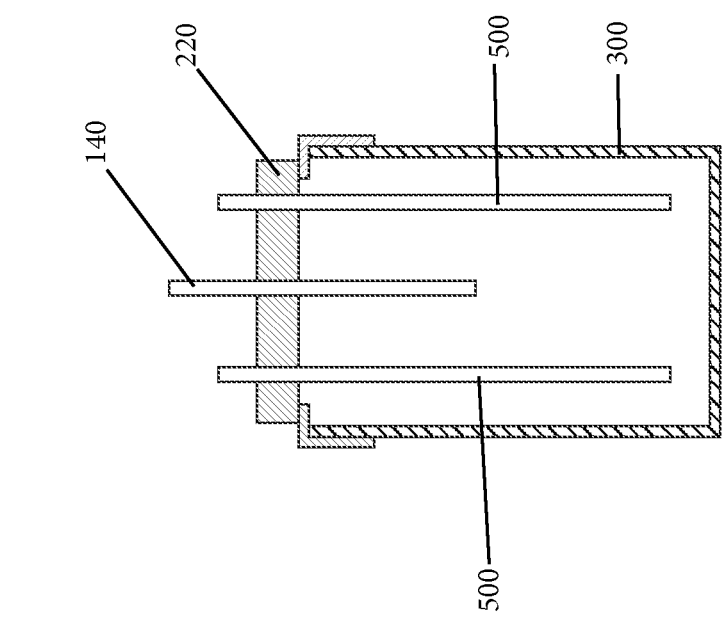
FIG. 2 is side view of the entire bioreactor design including a jig for alignment of external and internal components of the hCOC mold.

In accordance with the present invention and as shown in FIGS. 3A and 3B, a second support member (cover) or first jig 220 is provided to mate with an open end of a vessel or container, such as first mold container 152. The second jig 220 is designed to cover the first mold container 152 and another vessel used subsequently as described below. The second jig 220 has a top surface 222 and side walls 224 (which can be fitted over the side walls of the vessel 300). The top surface 222 has a plurality of openings formed therein. In the illustrated embodiment, the second jig 220 has three openings 230, 232, 234 formed therein, with the second opening 232 being the middle one.

It will be appreciated that the openings 230, 232, 234 do not have to have the same characteristics (shapes and/or dimensions) and in the illustrated embodiment, the opening 232 is different than the openings 230, 234. More specifically, the opening 232 which represent a middle opening between the openings 230, 234 is larger (greater diameter) than the openings 230, 234.

As with the first jig 200, the second jig 220 has a lock mechanism for securely positioning and retaining members (tools/instruments) that are inserted into any one of the openings 230, 232, 234. For example, a plurality of set screws 240 can be used and in particular, the set screws 240 pass through one or more of the side walls 224. In the illustrated embodiment, the set screw 240 for the middle opening 232 passes through one side wall 224, while the other two set screws 240 for the openings 230, 234 pass through an opposite side wall 224 to facilitate unencumbered manipulation of individual set screws 240. The set screws 240 can be in the form of nylon screws to avoid corrosion and minimize damage to inserted tools/instruments.

The middle opening 232 is constructed to receive the cannula 140. The distal end of the cannula 140 is thus passed through the middle opening 232 so as to position the distal end of the cannula 140 below the second jig 220. It will be appreciated that the cannula 140 includes the first ring 130 and the O-ring 135 (both of which are disposed at or near the distal end of the cannula).

Figure 8:
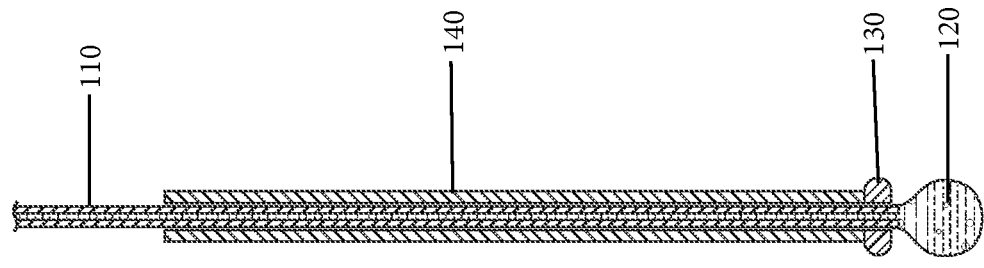
FIG. 8 is a cross-sectional view showing the balloon of the catheter inflated.
Figure 7:
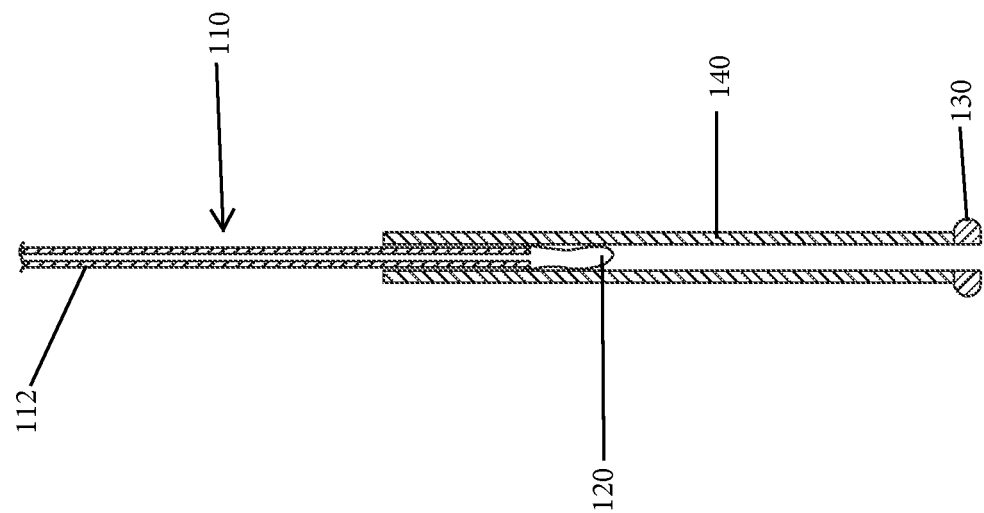
FIG. 7 is a cross-sectional view showing a balloon catheter being threaded through a lumen of a cannula.

To further prepare the engineered cardiac organoid chamber, the catheter 110 is passed through the lumen formed in the cannula 140. The balloon 120 is in a deflated state as the catheter 110 is passed through the lumen (FIG. 7). The catheter 110 is advanced through the lumen until the balloon 120 extends beyond the open distal end of the cannula 140. The balloon 120 is then inflated as by injecting an inflation fluid (e.g., deionized water) into the balloon 120. After the balloon 120 is inflated, the catheter 110 is gently pulled back so as to position the inflated balloon 120 against the distal end of the cannula 140 (FIG. 8). The inflated balloon 120 thus lies directly below the first ring 130 (support ring).

The set screw 240 can be used to secure the cannula 140 in place relative to the second jig 220.

The catheter 110 is typically a flexible member that is sized to be slightly smaller than the lumen of the cannula and therefore, a frictional coupling can be formed between the catheter 110 and the cannula 140. In any event, the catheter 110 slidingly travels within the lumen of the cannula 140 to permit repositioning thereof as well as insertion and removal of the catheter 110.

Once the catheter 110 is in the desired position described above relative to cannula 140, the catheter 110 can be secured in the desired position using a retaining mechanism. For example, a clamp 250 or the like can be used to hold the catheter 110 in place or a set screw can be used to apply tension on the catheter 110 that is within the lumen of the cannula 140. Alternatively, a frictional fit can exist between the catheter 110 and the cannula 140 and thus, the catheter 110 is frictionally held in place within the cannula 140. The above techniques assist in maintaining alignment of the inner balloon 120 within the outer agarose mold 150 as described above and further detailed below.

Once the balloon catheter 110 is secured in the desired location with the balloon 120 being inflated, the second jig 220 is then inserted into the first mold container 152 that contains the formed cup-shaped agarose mold 150. The inflated balloon 120 can then be further manipulated where needed to position the balloon 120 in a target location in the cup-shaped mold cavity. For example, the balloon 120 can be centered within the mold cavity such that there is approximately 2 mm of space, uniformly distributed, between the agarose wall and the balloon 120. The volume of the balloon 120 can also be adjusted to increase or decrease this gap spacing, which ultimately determines the wall thickness of the resulting organoid chamber. Additionally, the position of the second jig 220 can be adjusted and in particular, the second jig 220 can be positioned at angle to aid in alignment of the balloon 120 within the mold cavity. The balloon 120 is also lowered within the mold cavity 155 until it is at a target location. For example, the balloon 120 can be lowered until the balloon 120 is disposed approximately 2 mm from the bottom of the agarose mold. The balloon 120 can thus be concentrically located within the mold 150. It will be appreciated that the 2 mm sized spacing mentioned above is merely exemplary and not limiting of the present invention since in different applications, the dimension of this spacing can be different than 2 mm. For example, the balloon 120 can be spaced (uniformly) from the mold a distance between about 0.5 mm and about 3 mm. The gap is shown in an exaggerated state in the figures to allow the balloon and side walls of the mold cavity to be seen.

Preparation of Cells and Tissue Solution

In accordance with the present invention, human cardiomyocytes (hCMs) are used as part of the process for forming the human engineered cardiac organoid chamber (hCOC). As described in greater detail below, an ice-cold sterile collagen solution is prepared using purified bovine dermal type 1 collagen. This gel is mixed with Matrigel basement membrane matrix and a cell suspension according to a predetermined ratio. This results in a cold cell-matrix solution being formed and the detailed Example set forth below describes the detailed steps for creating one cold cell-matrix solution.

One of the unoccupied openings 230, 234 can be used as a media access port or a dedicated port 235 can be formed for delivering the cold cell-matrix solution (tissue culture mixture) into the mold cavity 155 using a suitable instrument (FIG. 1A). For example, a pipette (e.g., a 1000 mL pipet) can be used to deliver the cold cell-matrix solution. The cold cell-matrix solution thus flows around the inflated balloon 120 and is contained within the mold cavity 155 defined by the gap space between the outer cup-shaped mold 150 and around the inflated balloon 120 and the cannula 140. The first ring 130 is to be entirely submerged in the cold cell-matrix solution and thus, the axial position of the balloon 120, or the volume of the cold cell-matrix solution, can be adjusted to ensure that the first ring 130 remains submerged. The first ring 130 serves to prevent tissue slippage during tissue culture.

The entire assembly is then incubated under prescribed conditions that result in initiation of collagen gel polymerization. For example, the assembly can be incubated at 37° C. in 20% $O_2$, 5% $CO_2$ and 95% ambient humidity for two hours. In addition, the tissues can be "floated" two hours later by adding enough neonatal bovine serum (NBS)-supplemented culture media to completely submerge the tissue and then the assembly can be returned to the incubator (FIG. 1A).

Maintaining the Tissues in the Bioreactor

After a predetermined period of time passes (e.g., 48 hours) and the tissue has undergone self-assembly construction within the mold cavity of the first mold container 152, the jig assembly (defined by the jig 220 and attached cannula 140 and balloon catheter 110) is removed from the mold cavity 155. The jig assembly is then placed on top of a second container 300 which can be similar or identical to the first mold container 152 with the exception that the second container 300 does not include an agarose mold and instead is empty. The dimensions of the second container 300 can be the same as the first container 152. The second container 300 is also sterilized prior to mating the jig assembly to the open top of the second container 300.

A culture media is then added to the second container 300 through the media access port (e.g., opening 235) formed in the second jig 220 (FIG. 1B). Half of the culture media is renewed daily.

As the tissue is prepared in the culture media contained within the second container 300, the balloon 120 remains inflated and the first ring 130 remains immediately above the inflated balloon 120 and surrounds the cannula 140. The second container 300 with the culture media is maintained in the incubator for a predetermined period of time, such as 7 to 10 days. During this time, the myocytes begin contracting and forming a coordinated network as the engineered tissue becomes compacted around the balloon 120. In other words, an engineered cardiac organoid chamber is generated around the balloon 120 and once the balloon 120 is removed, an organoid 199 (FIG. 1C) remains in place and is sealingly coupled to the first ring 130 disposed about the cannula 140.

In accordance with the present invention, beating cardiac chambers (cardiac organoids) were created from human cardiac cells. The present invention combines organoid chamber engineering techniques with human cardiomyocytes derived from pluripotent stem cells. This combination results in a unique human beating heart chamber that provides a new bridge between traditional in vitro culture systems and preclinical testing in animals and human patients.

Testing Properties of the Tissue (e.g., Organoid Pump Function)

After a predetermined period of time, such as 7-10 days of culture, the spontaneously beating cardiac organoid is prepared for testing. In particular, pacing and mapping experiments can be performed beginning at around day 7 to 10. The catheter 110 is removed from the jig assembly by first deflating the balloon 120 carefully while leaving behind the cardiac organoid. The clamp 250 (FIG. 1C) is loosened to allow for removal of the catheter 110. One technique for removing the catheter 110 is to gently twist the catheter 110 back and forth to check for any attachment of the tissue to the balloon 120. If any attachment of the tissue is noticed, the tissue can be returned to the incubator for 15 minutes as this usually helps the tissue detach from the balloon 120.

The catheter 110, with balloon 120 deflated, is then gently withdrawn (removed) out of the open proximal end of the cannula 140 (see FIG. 1C). A small amount (100-200 µl) of NBS media can be added to the open proximal end of the cannula 140 as the catheter 110 is removed. Often, a vacuum forms in the mold cavity (chamber) as the catheter 110 is removed. Adding the NBS media can help mitigate the vacuum if formed. Additionally, as the catheter 110 is removed, the catheter 110 can be twisted back and forth as this also aids in releasing any vacuum.

Preferably, the tissue (cardiac organoid) is tested in a closed-loop system 400 such as the one shown in FIG. 9 (which is a schematic of one exemplary organoid function testing system). The system 400 includes the bioreactor 100 and in particular, the second container 300 that is filled with culture media with the organoid shown at 199. Unlike the conventional technique in which the organoid was physically removed from the balloon catheter and then sutured or otherwise attaching to a test instrument, the organoid 199 generated according to the teachings of the present invention is grown in-situ about the cannula 140 and in particular, the organoid 199 is attached to the cannula 140 via the porous support ring 130 and the water-tight O-ring seal 135 to prevent fluid leakage.

A connector 410, such as a T-connector, is sealingly and fluidly connected to the open proximal end of the cannula 140. The connector 410 thus has a first leg 412 and a second leg 414 to which other objects can be attached. An open fluid reservoir 420 is sealingly connected to the first leg 412 by a conduit 430. The open fluid reservoir 420 contains the culture media and can include additional substances, such as phenol red to enable pH to be monitored and enhance the organoid image contrast. The conduit 430 can be in the form of flexible tubing which allows flow of the culture media.

The mean chamber pressure (within the organoid 199) can be controlled by adjusting the height of the open fluid reservoir 420 and in particular, the open fluid reservoir 420 can sit on an adjustable platform (jack 425) that allows the height of the reservoir 420 to be adjusted (e.g., manually or via motor control) to control the hydrostatic pressure load on the organoid 199. Chamber pressures are measured relative to the external reservoir 420 using a suitable pressure transducer 440, such as an indwelling electronic pressure transducer. The transducer 440 has a probe element 442 that passes through the second leg 414 and through the lumen of the cannula 140 into the center of the organoid 199. The probe element 442 is sealed to second leg 414 with a suitable sealing material 415, such as a wad of malleable gum to maintain a closed fluid connection via the conduit 430 which is connected to the open fluid reservoir 420. The resulting passive and active pressures within the organoid chamber are recorded by the pressure transducer 440 to assess contractile function. A high-speed video camera (digital camera) 450 is used to monitor changes in organoid size synchronized with the pressure recordings.

For electrophysiologically controlled measurements of contractile performance, or for chronic electrical stimulation during organoid culture, a pair of electrodes 500 (connected to an electrical stimulator apparatus) is used to electrically pace the organoid chamber using a technique known as electrical field stimulation. The electrodes 500 are received through openings 230, 234 formed in the top of the second jig 220. Since the openings 230, 234 are at a fixed, spaced relationship relative to the opening 232, the electrodes 500 are maintained at a fixed position and spaced a fixed distance from the cannula 140 (and thus from the organoid), to ensure a well-defined electrical field gradient during pacing. Any number of techniques can be used to securely attach or couple the electrodes 500 to the second jig 220, such as nylon set screws 240. As shown in the figures, the electrodes 500 depend downwardly into the culture media and are at least generally parallel to the cannula 140. The electrodes 500 can be selected from any number of suitable conductive and non-corrosive electrode materials, including carbon rod electrodes. The electrodes 500 are thus proximate and spaced from the organoid 199 that is attached to the first ring 130 at the distal end of the cannula 140.

A resulting extracellular electrogram can be recorded using conventional devices, such as a microelectrode AC amplifier that includes a band-pass filter and is sampled at a predetermined frequency. Extracellular voltage, chamber pressure, and digital video can be acquired simultaneously using an A/D converter on a personal computer. Chamber cross-sectional area can be measured from the digital video by applying grayscale threshold and automatic detection of the tissue boundary using suitable image processing software, such as ImageJ.

Figure 10:
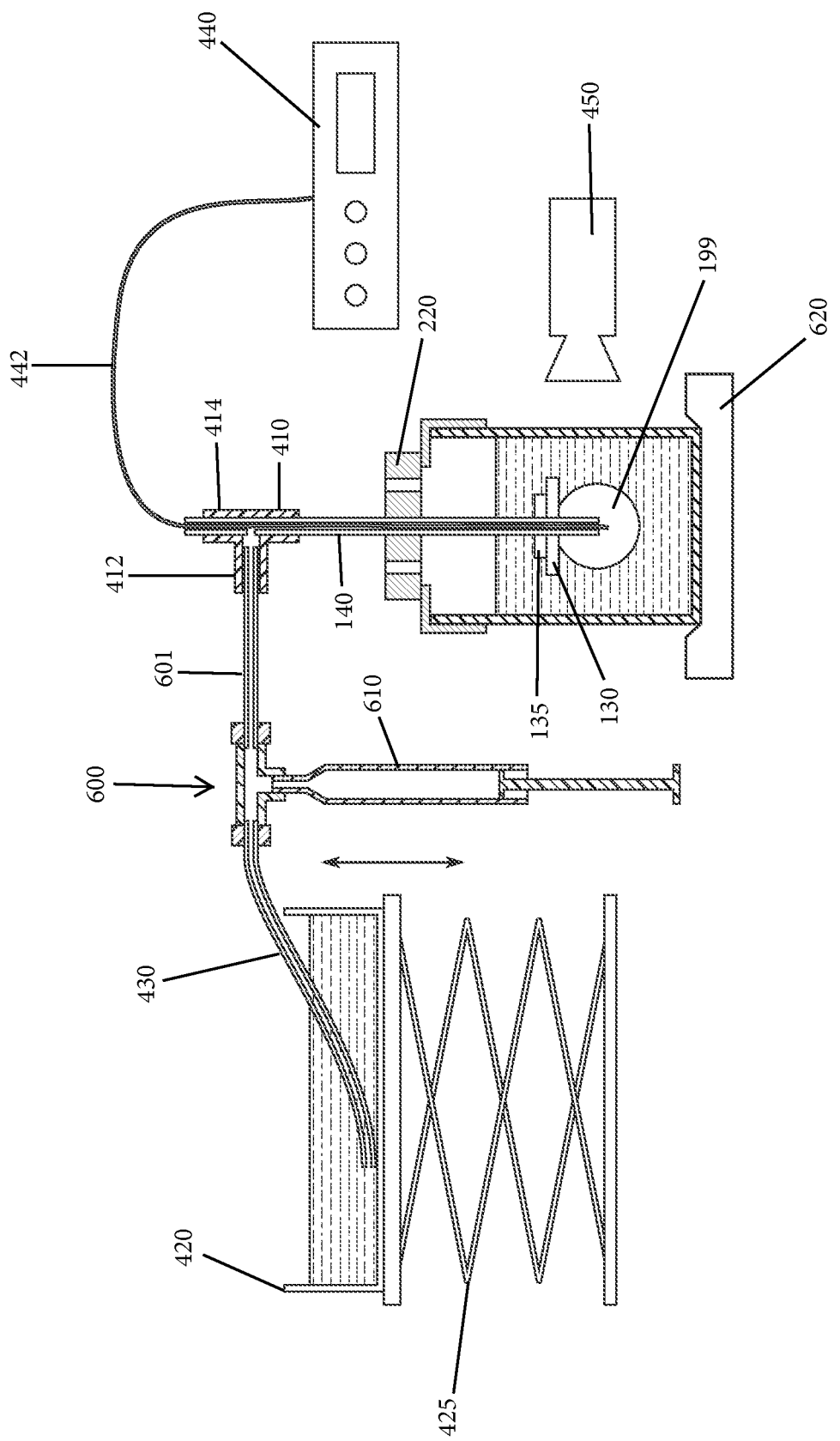
FIG. 10 is a schematic of another exemplary organoid function testing system.
Figure 11:
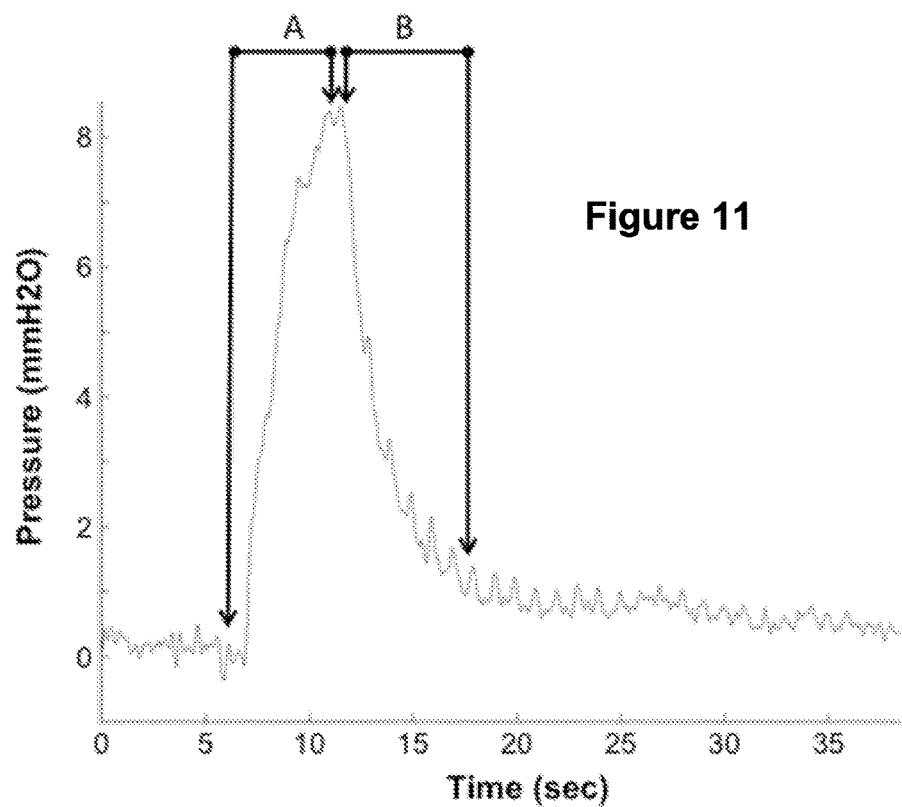
FIG. 11 is a graph showing the organoid chamber pressure versus time during a test without the rubber O-ring seal in place.
Figure 12:
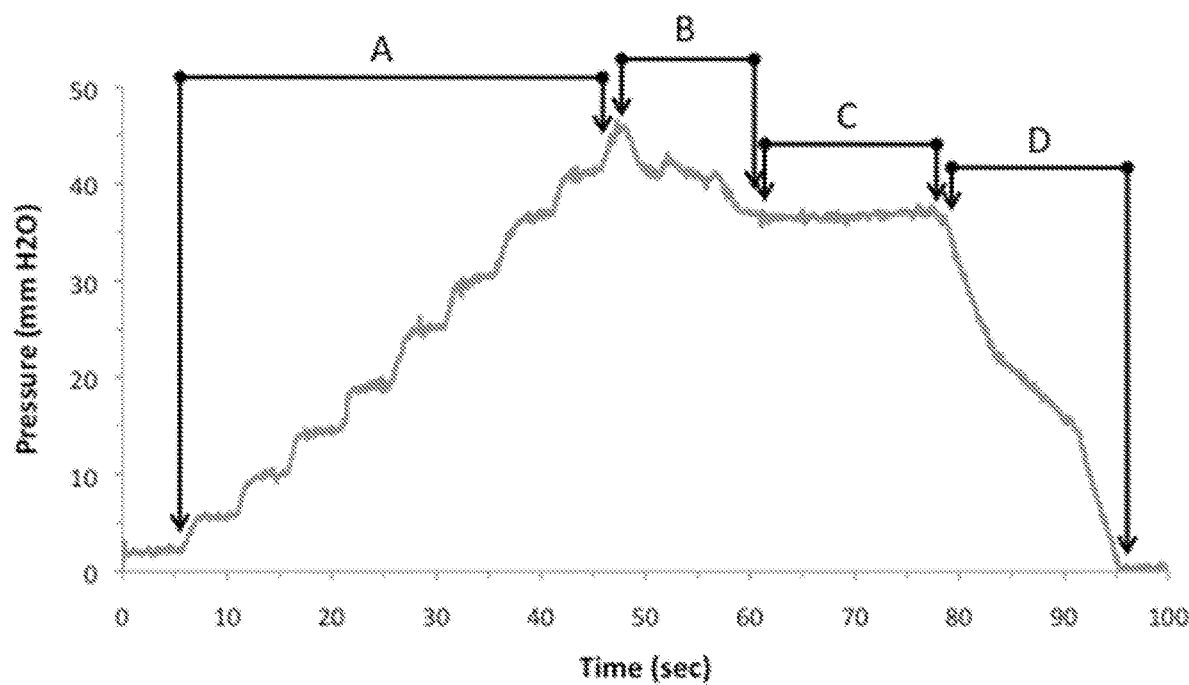
FIG. 12 is a graph showing the organoid chamber pressure versus time with the rubber O-ring seal in place.

The following graphs show pressure within the organoid chamber versus time without the O-ring seal 135 (FIG. 11) and with the O-ring seal 135 (FIG. 12). The pressure data are measured using a Millar Mikro-Tip pressure transducer threaded through the cannula 140 and into the organoid lumen, with the end of the tube/transducer sealed with modeling clay to create a closed fluid system (FIG. 10). The data in FIG. 11 clearly shows that without the O-ring seal 135, the pressure load on the organoid can be increased but it rapidly falls as the fluid leaks out of the system. To identify the source of the leak, we added dye to fluid within the chamber to visualize that the fluid was leaking at the interface between the porous support ring 130 and the rigid tube 140. When the O-ring 135 was added to create a water-tight seal at this interface, then we were able to increase the lumen pressure to higher levels and hold the pressure steady to allow measurements at controlled loading pressures (FIG. 12). This is essential to accurately evaluate the load-dependent pump function of the organoid chamber, which is a fundamental and clinically relevant characteristic of natural heart pump function. We have also demonstrated optical mapping of electrical activation waves over the surface of the organoid chamber using voltage sensitive fluorescent dyes (FIG. 13).

FIG. 11: Organoid chamber pressure versus time during example test without the rubber O-ring seal in place. When the pressure is increased by about 8 mmH2O (Region A), the pressure is not held steady, and rapidly falls back toward baseline in less than 10 seconds (Region B) due to fluid leaking out of the chamber. Note that oscillations in the pressure signal are due to beating of the organoid during testing. Accurate analysis of these oscillations is greatly hampered by the non-steady nature of the loading pressure.

FIG. 12: Organoid chamber pressure versus time during example test with the rubber O-ring seal in place. Region A shows incremental step loading of approximately 5 mmH2O every 5 seconds from baseline of about 2 mmH2O up to 40 mmH2O. The steady regions after each increment demonstrate that the closed system is able to hold constant pressures. After some adjustment near the maximum (Region B), the pressure was reduced to approximately 35 mmH2O and held steady for about 20 seconds (Region C), indicating no appreciable fluid leakage in the system. The pressure was then rapidly reduced back to zero at the end of the test (Region C), indicating an ability to accurately control the organoid chamber pressure over a wide range. Note the difference in scale for both the pressure axis and the time axis in FIG. 11, which is very zoomed in compared to FIG. 12.

Figure 13:
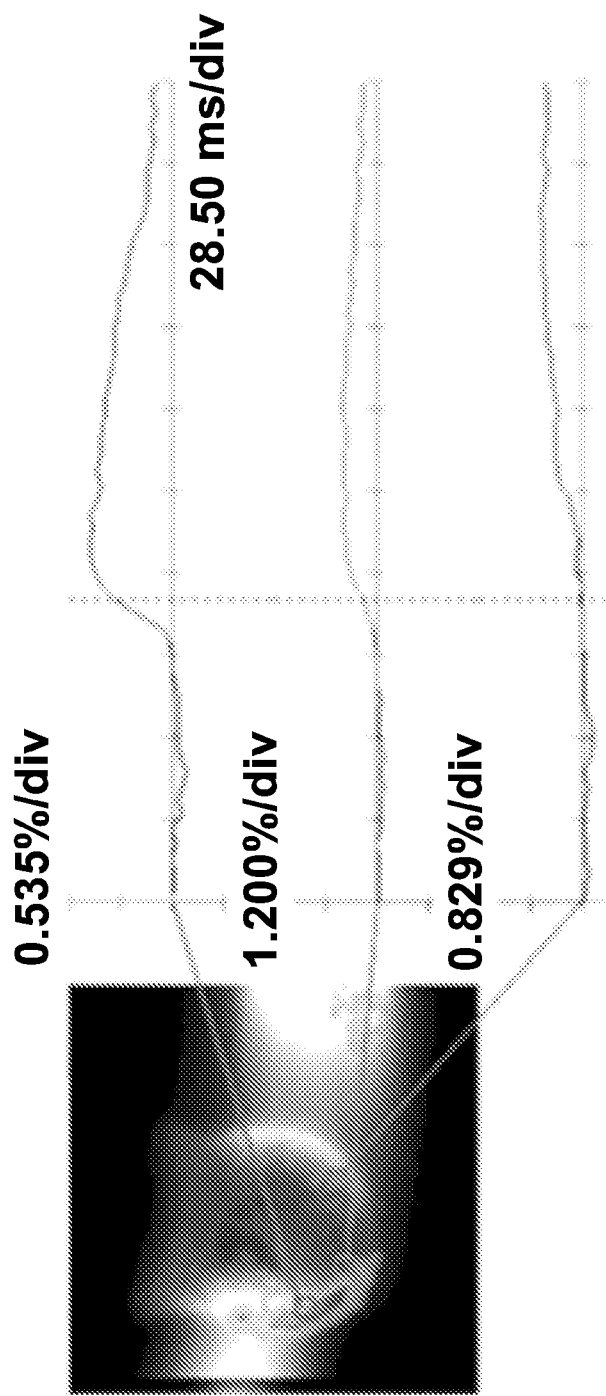
FIG. 13 is a graph showing the organoid chamber during optical mapping of electrical signals.

FIG. 13: Organoid chamber during optical mapping of electrical signals. The image shows pseudo-color of fluorescence intensity using voltage-sensitive fluorescent dye (di-4-ANEPPS), with individual tracings of signal intensity (i.e. voltage) vs. time at multiple sites on the organoid, indicating propagation of the electrical wave from left to right.

Advantages of the Bioreactor System

The construction of the bioreactor 100 and related equipment overcomes the deficiencies associated with the conventional equipment in that the organoid chamber is grown directly on an instrument, in this case the cannula 140, that is configured to be used in the testing phase as well as the initial culturing phase in which the organoid is generated. The construction of the bioreactor 100 of the present invention thus avoids the need to physically detach the organoid from the balloon catheter and then transfer and attach the organoid to a test instrument, such as pressure transducer equipment, using a suture or similar method—this process often results in damage to the organoid and compromises sterility and viability of the living engineered tissue.

The human organoid chambers and the related bioreactor systems disclosed herein have a vast number of practical applications for creating functional in vitro models the human heart with biomimetic structural and functional properties for enhanced drug/toxicity screening and other (cell, gene) therapeutic discovery/preclinical testing applications. Accordingly, by creating a biomimetic in vitro surrogate for the human heart, the present technology helps bridge the longstanding gap between traditional cell culture systems and in vivo animal models and eventual clinical trials. The present invention essentially provides an in vitro preclinical human organ model with reduced and controlled biocomplexity for improved screening applications that can improve the efficiency and success rate of novel or repurposed drugs. Creating tissues from human adult pluripotent stem cells (e.g., iPSCs) can even allow patient-specific personalized drug screening for individual assessment of efficacy or toxicity.

The human organoid chambers generated using the bioreactor systems disclosed herein are also uniquely suitable when clinically relevant pressure-volume characteristics are required, or when optical mapping of electrophysiological characteristics is of interest.

3D Cell Alignment

In accordance with the present invention, 3D cell alignment is generated by silicone balloon surface patterning. More specifically, various surface patterns can be formed on the outer surface of the balloon 120. These textured balloons induce cell and matrix alignment in the 3D organoid chambers, more like the natural heart wall. The resulting anisotropy fundamentally impacts the structural organization of the tissue as well as the resulting mechanical properties and electrical conduction properties, providing a novel strategy to improve overall pump function of the organoids.

EXAMPLES

The following examples are provided to better illustrate embodiments of the present invention. However, it is to be understood that these examples are merely illustrative in nature, and that the process embodiments of the present invention are not necessarily limited thereto.

Preparation of the Cells

The hCMs are ready for use after the single cells have re-aggregated into small clusters of cells (such as a cluster of 15-20 cells). The plate on which the hCMs are present should be inspected prior to cell transfer and is a substantial number of cells have attached to the plate, the cells can be scraped with a cell lifter, such as a Corning cell lifter. The cell/tissue culture is then further prepared by performing the steps of: pelleting the cells (300×g for a selected time period (e.g., three minutes)) and then aspirating off the supernatant, leaving approximately 500 μL of solution (resulting solution). The supernatant is then resuspended in the 500 μL of solution and is transferred to a different vessel, such as an Eppendorf tube. The cells undergo a pelleting procedure again (200×g) in a microfuge for a predetermined period of time (e.g., 5 minutes). The resulting solution (tissue culture) is then set aside.

Conventional protocol can be followed to prepare the hCMs for the present use. After an incubation has passed (e.g., 48 hours), the cells are transferred to a centrifuge tube (e.g., a 15 ml tube).

Preparation of the Tissue

1. Thaw the Matrigel on ice first thing in the morning (or on ice at 4° C. overnight);
2. Put all reagents on ice (collagen, NaOH, 10×PBS, sterile water, HEPES, 10×MEM, matrigel);
3. Open the excel document "Human Tissue Strip Calculations" (a software application)
4. Under the tab "Start Here," enter the total number of tissues desired, the tissue volume (usually 1.2 mL) and the desired cell concentration (usually 10 million hCMs/mL);
5. Click on the tab "Final Solution" to view the components of each mixture. You will create three solutions in three tubes: 1) a dilution of the collagen, Collagen Dilution; 2) a mixture of the collagen with MEM and HEPES, Collagen Mix; and 3) the final tissue mix containing the cells, Tissue Mixture. The final tissue mixture is composed of 2 mg/mL bovine type I collagen and 0.9 mg/mL Matrigel;
6. Under the "Final Solution" tab in the excel document, tissue mixture appears twice. The first set, Tissue Mixture (known [cell]), will give you the amount of each component if you know your cell concentration. With hCMs this can be quite difficult. Instead, the second set, Tissue Mixture (known cell number), can be used and which will tell you the volume in which to re-suspend the hCMs in order to achieve the correct cell concentration for the tissues. However Tissue Mixture (known cell number) is dependent on knowing the total number of cells in the solution. Typically, one assumes that all 2 million cells from the re-aggregation survive to the tissue stage, so there will be 2 million cells per re-aggregation plate;
7. Create each solution using the volumes prescribed in the excel document. Typically the components can be added in the order from top down (e.g., collagen then 10×PBS then 1M NaOH then sterile water for the collagen dilution solution);
    a. If using Tissue Mixture (known cell number), remove all of the supernatant from the hCM cell pellet (see section II, step 5) by gently pipetting off the supernatant with a p20 pipet and replace with the media volume described in Tissue Mixture (known cell number).
    b. It is possible to add the 10×MEM and HEPES directly to the collagen dilution to create the collagen mix. This avoids an extra pipetting step that may introduce error.
    c. Note: Depending on the lot of Matrigel used, it may be necessary to change the "Matrigel Stock Concentration" under the tab "Tissue Mix." Usually it is necessary to phone the vendor to obtain the lot's Matrigel concentration.
    d. Note: For 1 chamber (1.2 ml) these volumes are typically:
        Collagen Dilution
            0.75 mL Collagen Stock (5 ml/ml)
            0.12 mL 10×PBS
            0.019 mL 1M NaOH
            0.311 ml sterile deionized water
        Collagen Mix
            1.056 mL Collagen Dilution (above solution)
            0.132 mL 10×MEM
            0.132 mL HEPES (pH 9)
        Final Tissue Mix
            1.056 mL Collagen Mix (above solution with MEM and HEPES)
            0.113 mL Cardiomyocytes (Resuspend cell pellet in this volume)
            0.150 mL Matrigel Forming an Exemplary Closed Loop Testing System (FIG. 10)

To form the closed loop:
1. Attach the flexible tubing (from the muscle bath) to either end of a 3-way Luer lock valve 600.
2. Attach a 20 mL syringe 610 to the third outlet of the Luer-lock.
3. Fill a large petri dish or beaker 420 with culture media and place it on an adjustable jack 425.
4. Place the open end of one of the tubes into the media in the reservoir and open the valve between the syringe and the reservoir.
5. Draw media back into the syringe through the tubing, being sure to avoid any air bubbles entering the tubing as you draw back.
6. Close the valve 600 to the reservoir 420 and open it between the syringe 610 and the second set of tubing 601.
7. Connect the second set of tubing 601 to the T-connector 410 (the stem 412 of the T).
8. Pass the pressure transducer 442 through the T-connector 410 so that it exits the other side.
    a. Note: The transducer will eventually enter the lumen of the chamber, so it can be helpful to pre-measure the distance necessary for the transducer so that it sits appropriately through the T-connector, but also will sit in the lumen of the chamber once everything is connected (distance for transducer to travel=distance T-connector+distance hypodermic tubing).
9. Close the open space between the pressure transducer and the T-connector with a sealant, such as modeling clay or the like. The T-connector should now only have one end open, with the transducer sticking out of it.
10. Draw media through the second set of tubing 601, again being sure to avoid entry of air bubbles. The media should be traveling through the open end of the T-connector, so be sure it is submerged.
11. Remove the top of the chamber bioreactor 100 and place it in the media.
12. Submerge the chamber and tubing in media, being sure to remove any air bubbles that may be in the tubing. It may be necessary to submerge the entire top of the bioreactor, which is fine. The most important thing is to make sure all air is removed from the hypodermic tubing.
13. At this time, also check the position of the O-ring 135 and move it to touch the top of the PPE ring if necessary.
    a. Note: The O-ring helps seal the gap between the PPE ring and the hypodermic tubing, to ensure that maximum pressure is generated in the closed system and is detected by the transducer.
14. Connect the open end of the T-connector to the hypodermic tubing so that the probe of the pressure transducer is in the lumen of the chamber.
15. Reconnect the top of the bioreactor to the bottom half of the bioreactor.
16. Place the bioreactor on a heated stage 620, on an adjustable jack in front of a high-speed camera 450.
    a. Note: The pressure into the lumen of the chamber will be determined by the difference in height between the fluid in the larger reservoir, and the fluid in the bioreactor. Thus, the fluid levels in the bioreactor and the open fluid reservoir should be equal.
17. If needed, thread the carbon electrodes through their designated holes in the top of the bioreactor and connect them to a Grass stimulator.

Once the closed loop system has been established, the following tests can be performed in NBS media:
1. Establish baseline function
    a. Measure pressure over time at spontaneous, 0.5, 1, 1.5, 2.0, 2.5, 3.0 Hz
        i. Capture both pressure and volume data at each frequency so P-V loops can be reconstructed
        ii. Use volume data for estimated ejection fraction calculations
        iii. Use pressure data for pressure vs time for each frequency (shows capture and ability to pace)
    b. Measure change in developed pressure versus luminal pressure at set frequency (I suggest 1, 1.5 or 2 Hz)
        i. Increase height of fluid reservoir by 5 mm increments and record video and pressure for 20 s per step for a maximum of 40 mmH2O
        ii. This data will permit developed pressure versus luminal pressure graphs and thus test for an active Frank-Starling mechanism 2. Establish effect of pharmacologic agents on chamber function (e.g., $CaCl_2$, Isoproterenol, Verapamil)
    a. Repeat "a" and "b" above, but in the presence of pharmacologic agents
        i. From this, changes in pressure output, Frank-Starling response and pressure-vole loops from pharmacologic agents can be evaluated
    b. Note: For known β-adrenergic agonists, spontaneous frequency changes will be important, but to control for frequency effects, also be sure to collect data at set frequencies (e.g., 1, 1.5 or 2 Hz).

Additional Bioreactor Details:
Cannula 140
The cannula 140 can have one or more of the following features/properties:
  outer diameter (OD) must be smaller than diameter of final organoid balloon 120;
  inner diameter (ID) must be large enough to allow pass through of the deflated balloon catheter 110 and later the pressure transducer (e.g. Millar Mikro-Tip or similar) for measuring chamber lumen pressure;
  material must be stiff/rigid to hold balloon 120 precisely in place during organoid culture;
  inner wall of the cannula 140 should be smooth to allow catheter and transducer to pass easily;
  outer wall can be smooth or rough but must hold porous support ring (first ring 130) for growing the organoid, and O-ring seal 135 for pressure—to make a good seal with the O-ring 135, it is probably preferable for the outer surface to be smooth
  the geometry of the cannula 140 can be straight, or could have an integrated flare or flange or similar feature near the bottom end, against which the porous support ring 130 can be pressed to help hold the water-tight seal;
  the bottom tip of the rigid cannula 140 is slightly tapered to facilitate fitting the stiff porous support ring 130 onto the end of the cannula 140, especially if the ring/organoid needs to be removed or happens to accidentally fall off the rigid cannula 140 during organoid testing; and
  the cannula 140 can be formed of other materials including polystyrene or polycarbonate tubes or various biocompatible metal alloy tubes of comparable ID/OD dimensions.

Porous Support Ring 130
The porous support ring (first ring 130) can be in the form of a ring that is formed (cut/stamped) from a ¹⁄₁₆" thick sheet of hydrophilic-treated porous polyethylene with 70-um pore size; however, the first ring 130 can be formed from other suitable materials and have other properties.
The porous support ring 130 can have one or more of the following features/properties:
  hydrophilic so that a collagen/cell solution will wick into the material when wet—can be hydrophobic and then chemically treated (e.g. with sulfuric acid) to make hydrophilic;
  readily sterilized by UV or gas sterilization;
  pore size large enough to allow solution and cells to freely wick into the material, but small enough to provide large surface area and many points of contact for firm adhesion to organoid during culture. We have successfully tested pore sizes in the range of 50 to 150 um;
  thick enough to provide needed structural stability but not too thick to absorb excess cell/matrix solution (e.g., ¹⁄₁₆" and ⅛" thicknesses);
  rigid enough to grab with tweezers and provide structural support for the organoid, but soft enough to cut into a spherical shape and punch a hole to fit the rigid tubing.

Not too brittle, or it may snap/crumble when press-fit onto the rigid cannula tubing 140;

Inexpensive and disposable—too difficult/impractical to clean and reuse;

Other textured substances, including other porous plastics (e.g. polystyrene) and some porous metals (e.g. nickel foam), may be reasonable alternatives to the porous polyethylene.

In one exemplary embodiment, the first ring 130 can be cut from 1/16" thick sheet of hydrophilic-treated porous polyethylene with 70-um pore size.

O-Ring 135

In one exemplary embodiment, the O-ring 135 can be a silicone rubber O-ring with an inner diameter of about 5/64" and an outer diameter of about 13/64", with a thickness of about 1/16". The O-ring 135 can have one or more of the following features:

O-ring 135 must fit snugly on the cannula 140 (rigid tube) to form a water-tight seal, and also be flexible enough to press against the porous support ring 130 and form a water-tight seal;

Must be readily sterilized by ethanol, UV, gas or steam autoclave;

Preferably inexpensive and may be disposable; and

The O-ring 135 can be formed of other materials including neoprene, polyurethane, and other standard materials for commercial soft/flexible O-ring seals.

It will be appreciated that in an alternative embodiment, the O-ring 135 and porous ring 130 can be coupled to one another (at least temporarily) prior to coupling to the cannula 140.

APPENDIX A

Human Engineered Cardiac Organoid Construction
Reagents
Bovine Type I Collagen (Life Technologies, Cat # A10644-01)
10× Minimum Essential Medium Eagle (MEM) (Sigma, Cat # M0275)
Bovine Serum Albumin (Sigma, Cat # A9418)
High Vacuum Grease (Dow Corning) (Fisher Scientific, Cat #146355D)
PBS (Sigma, Cat # P3813)
Matrigel—hESC-qualified matrix (BD Biosciences, Cat #354277) in 150 μL aliquots
HEPES (Sigma, Cat # H4034)
Dulbecco's Modified Eagle's Medium (DMEM)—high glucose (Sigma, Cat # D5648)
Neonatal Bovine Serum (NBS) (Atlanta Biologics, Cat # S11250)
Penicillin-Streptomycin (Pen-Strep) (CellGro, Cat #30-002-CI)
Amphotericin B (Sigma, Cat # A2411-1G)
Agarose I (VWR, Cat #0710-25G)
Silicone caulking (Home Depot, Cat # GE281 3TG)
Solutions
2% BSA in PBS
0.2N HEPES, pH 9
1M NaOH
Sterile water
NBS media (DMEM, 10% NBS, 1% Pen-Strep, 0.2% Amphotericin B)
1×PBS
10×PBS
Materials
15 mL centrifuge tube (BD Falcon, Cat #352096)
Broad forceps (e.g., Fisher Scientific, Cat #10300)
Fine forceps (e.g., Fine Science Tools, Cat #11251-20)
Curved forceps (e.g., Fisher Scientific, Cat #12-460-518)
Black lab marker (VWR, Cat #52877-310)
Non-tissue culture treated 10 cm petri dish (Fisher Scientific, Cat #68-757-12)
20, 200 and 1000 μL pipets and pipet tips
polystyrene box, 3×3×6 cm (Container Store, Cat #60260)
hydrophilic porous polyethylene, 1.6 mm thick, 70 um pore size (Interstate Specialty
Products, Cat # POR-4899-ICA-01)
6-Fr Foley catheter (Cook Medical, Cat # G17203)
Rubber mallet (McMaster-Carr, Cat #5878A3)
11/32 stain-less steel hammer driven punch (McMaster-Carr, Cat #3424A24)
3 mL syringe (BD, Cat #309657)
Nylon screw compressor (Fisher Scientific, Cat #05-834)
13-mm glass test tubes (VWR, Cat #8900-480)
Optional:
Corning Cell Lifter #3008 (Fisher Scientific, Cat #07-200-364)

What is claimed:

1. A bioreactor system for preparing a cardiac organoid chamber and for subsequent testing thereof comprising:
a first vessel having a hollow interior and an open top;
a first cover for mating with the open top of the first vessel, the first cover having a first opening, a second opening, and a third opening, formed therein;
a cannula having a lumen that extends from an open first end to an open second end, the cannula being disposed within the first opening of the first cover such that a portion of the cannula, including the open second end, lies below the first cover within the hollow interior of the first vessel;
a porous ring coupled to the cannula at or proximate the open second end thereof; and
a balloon catheter having an inflatable balloon at a distal end of a catheter shaft, wherein the balloon catheter is adapted to pass through the lumen of the cannula when the balloon is in a deflated state, the balloon catheter being axially adjustable within the lumen to allow the balloon in an inflated state to be disposed adjacent: (1) the open second end of the cannula; and (2) the porous ring for preparing the cardiac organoid chamber about the inflated balloon and the porous ring; and
a pair of carbon rod electrodes disposed within the second and third openings for permitting electrophysiologically controlled measurements of contractile performance or chronic electrical stimulation during culture on the prepared cardiac organoid chamber.

2. The system of claim 1, wherein the first opening, the second opening and the third opening are formed in a top wall of the first cover wall, the first opening being formed between the second and third openings, wherein the pair of carbon rod electrodes are disposed within the second and third openings.

3. The system of claim 2, wherein the first cover has a means for securely coupling the cannula to the first cover.

4. The system of claim 3, wherein the means comprises a mechanical retaining member that holds and retains the cannula in a desired position within the first opening and relative to the first cover.

5. The system of claim 4, wherein the mechanical retaining member comprises a set screw that extends through a side wall of the first cover for applying a retaining force against the cannula.

6. The system of claim 1, wherein the cannula is formed of a rigid material.

7. The system of claim 1, wherein the cannula is formed of a material selected from a metal and a rigid plastic.

8. The system of claim 1, wherein the porous ring is formed of a hydrophilic porous polyethylene material.

9. The system of claim 1, wherein the porous ring is configured to prevent tissue slippage during tissue culturing to form the cardiac organoid chamber.

10. The system of claim 1, further including an O-ring disposed about the cannula and in intimate contact with a top surface of the porous ring, the O-ring being configured to provide a water-tight seal.

11. The system of claim 1, wherein the balloon catheter has a flexible shaft.

12. The system of claim 11, wherein the flexible shaft of the balloon catheter is frictionally fit within the lumen of the cannula to fix a relative position of the balloon catheter relative to the cannula.

13. The system of claim 11, wherein an external device is used to retain the balloon catheter within the lumen of the catheter such that the balloon catheter remains at a fixed location within the lumen with the inflated balloon being maintained adjacent the open second end of the cannula and the porous ring.

14. The system of claim 1, wherein the first cover has a means for securely coupling the pair of electrodes to the first cover.

15. The system of claim 14, wherein the means comprises a mechanical retaining member that holds and retains each electrode in a desired position within one of the second and third openings and relative to the first cover.

16. The system of claim 15, wherein the mechanical retaining member comprises a pair of set screws that extends through a side wall of the first cover for applying retaining forces against the respective electrodes.

17. The system of claim 1, wherein the cardiac organoid chamber is engineered from human cardiomyocytes derived from pluripotent stem cells.

18. The system of claim 1, wherein the inflatable balloon includes a surface pattern formed on an outer surface thereof for inducing cell and matrix alignment in the 3D prepared cardiac organoid chamber.

19. The system of claim 1, further including: a closed loop organoid function testing system that includes: a connector attached to the open first end of the cannula, the connector being fluidly connected to an open fluid reservoir by means of a conduit; a pressure transducer having a probe that can be passed through the lumen of the cannula after the cardiac organoid chamber is engineered and the balloon catheter is removed from the cannula, the probe having a distal tip that is positioned beyond the open second end of the cannula for placement within the cardiac organoid, the pressure transducer being configured to measure a chamber pressure within the engineered cardiac organoid chamber; and an imaging device for monitor changes in the size of the organoid.

20. The system of claim 19, wherein the imaging device is synchronized with the pressure transducer to allow changes in the organoid size to be synchronized with chamber pressure measurements recorded by the pressure transducer.

21. The system of claim 19, wherein the imaging device comprises a high-speed video camera.

22. A bioreactor system for preparing a cardiac organoid chamber and for subsequent testing thereof comprising:
a first vessel having a hollow interior and an open top;
a first cover for mating with the open top of the first vessel, the first cover having a first opening formed therein;
a cannula having a lumen that extends from an open first end to an open second end, the cannula being disposed within the first opening of the first cover such that a portion of the cannula, including the open second end, lies below the first cover and within the hollow interior of the first vessel;
a porous ring coupled to and disposed about an outer surface of the cannula at or proximate the open second end thereof;
an O-ring disposed about the outer surface of the cannula and in intimate contact with a top surface of the porous ring, the O-ring being configured to provide a water-tight seal; and
a balloon catheter having an inflatable balloon at a distal end of a catheter shaft, wherein the balloon catheter is adapted to pass through the lumen of the cannula when the balloon is in a deflated state, the balloon catheter being axially adjustable within the lumen to allow the balloon in an inflated state to be disposed adjacent: (1) the open second end of the cannula; and (2) the porous ring for preparing the cardiac organoid chamber about the inflated balloon and porous ring.

* * * * *

UNITED STATES PATENT AND TRADEMARK OFFICE
CERTIFICATE OF CORRECTION

| | |
|---|---|
| PATENT NO. | : 10,683,476 B2 |
| APPLICATION NO. | : 15/314870 |
| DATED | : June 16, 2020 |
| INVENTOR(S) | : Kevin David Costa, Timothy James Cashman and Peter Constantine Backeris |

It is certified that error appears in the above-identified patent and that said Letters Patent is hereby corrected as shown below:

In the Specification

Column 1
"Government Support Clause
This invention was made with government support under grant numbers HL085826 and HHSN26820100 awarded by the National Institutes of Health. The government has certain rights in the invention." should be added after the title.

Signed and Sealed this
Twenty-third Day of May, 2023

Katherine Kelly Vidal
*Director of the United States Patent and Trademark Office*